(12) United States Patent
Goulitski et al.

(10) Patent No.: US 10,863,922 B2
(45) Date of Patent: Dec. 15, 2020

(54) BI-FUNCTIONAL FILTER DEVICE FOR A GAS SAMPLING LINE AND SYSTEM

(71) Applicant: ORIDION MEDICAL 1987 LTD., Jerusalem (IL)

(72) Inventors: Konstantin Goulitski, Jerusalem (IL); Michael Kertser, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 218 days.

(21) Appl. No.: 16/186,192

(22) Filed: Nov. 9, 2018

(65) Prior Publication Data

US 2019/0133490 A1  May 9, 2019

Related U.S. Application Data

(60) Provisional application No. 62/583,583, filed on Nov. 9, 2017.

(51) Int. Cl.
*B01D 53/26* (2006.01)
*A61B 5/08* (2006.01)
*B01D 53/04* (2006.01)
*B01D 53/22* (2006.01)
*A61B 5/097* (2006.01)

(52) U.S. Cl.
CPC .............. *A61B 5/082* (2013.01); *A61B 5/097* (2013.01); *B01D 53/0415* (2013.01); *B01D 53/229* (2013.01); *B01D 53/261* (2013.01); *B01D 53/268* (2013.01); *B01D 2053/224* (2013.01); *B01D 2253/106* (2013.01); *B01D 2253/202* (2013.01); *B01D 2256/22* (2013.01); *B01D 2257/80* (2013.01); *B01D 2259/4533* (2013.01)

(58) Field of Classification Search
CPC .... A61B 5/082; A61B 5/097; B01D 53/0415; B01D 53/229; B01D 53/261; B01D 53/268; B01D 2053/224; B01D 2053/106; B01D 2053/202; B01D 2256/22; B01D 2257/80; B01D 2259/4533
USPC ................. 96/108, 117.5, 413, 417; 73/23.3
See application file for complete search history.

(56) References Cited

U.S. PATENT DOCUMENTS

| 4,370,152 | A | * | 1/1983 | Luper | B01D 53/261 95/281 |
|---|---|---|---|---|---|
| 5,575,832 | A | * | 11/1996 | Boyd | B01D 53/261 95/91 |
| 2019/0076057 | A1 | * | 3/2019 | Kertser | A61B 5/082 |

* cited by examiner

*Primary Examiner* — Frank M Lawrence, Jr.
(74) *Attorney, Agent, or Firm* — Cantor Colburn LLP

(57) ABSTRACT

A bi-functional filter device for removing liquid from a humid gas flowing through the filter device includes a filter body that includes an axial through-channel that passes lengthwise through the filter's body, through which gas (e.g., humid gas) can flow, and a dehumidifier sleeve that encloses the filter body. The filter body includes a capillary path that may absorb, and thus remove, liquids, for example laterally, radially or spirally (in spiral manner) from the through-channel of the filter body using capillary action, to thus clear the through-channel of the filter body from these liquids. The dehumidifier sleeve may evaporate liquid contained in (and arriving from) the filter body.

28 Claims, 8 Drawing Sheets

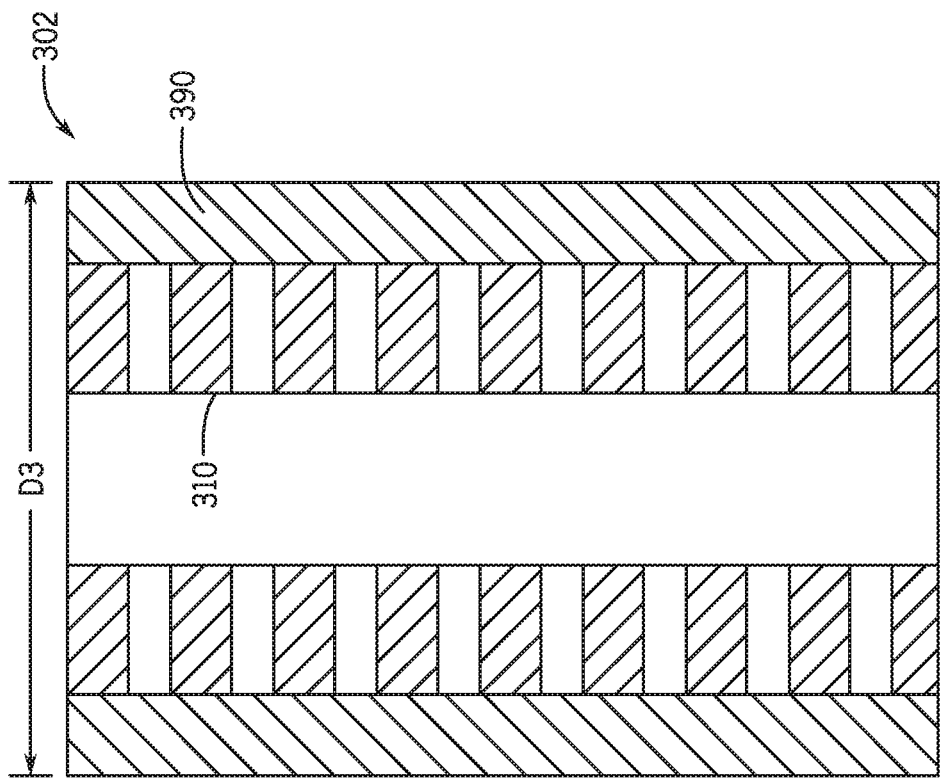
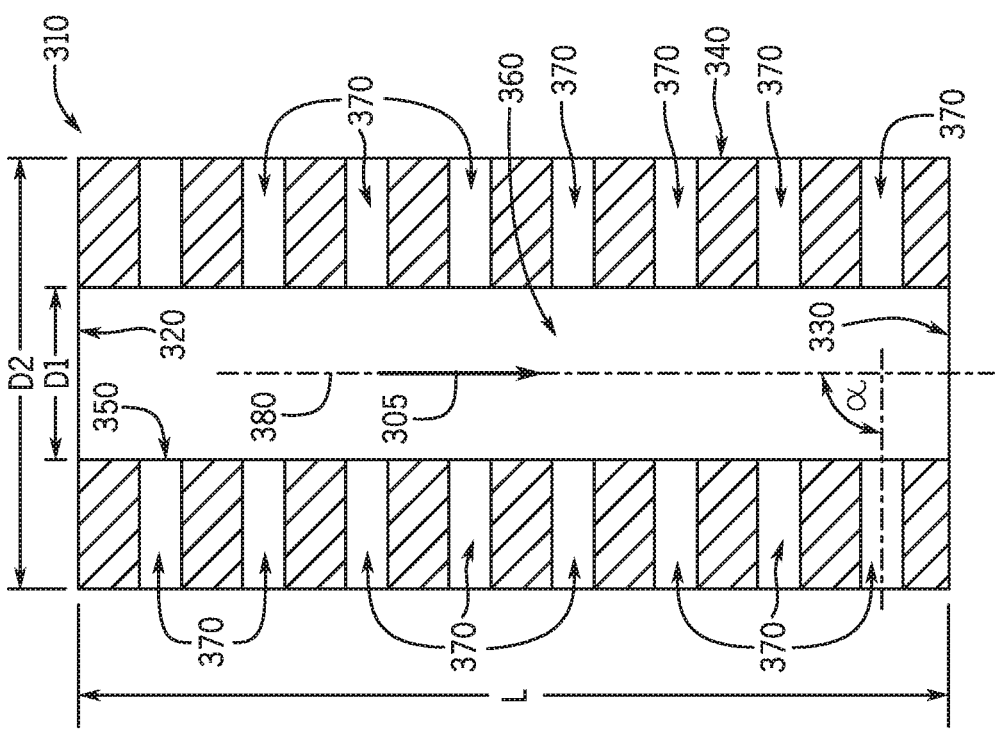
FIG. 3B
FIG. 3A

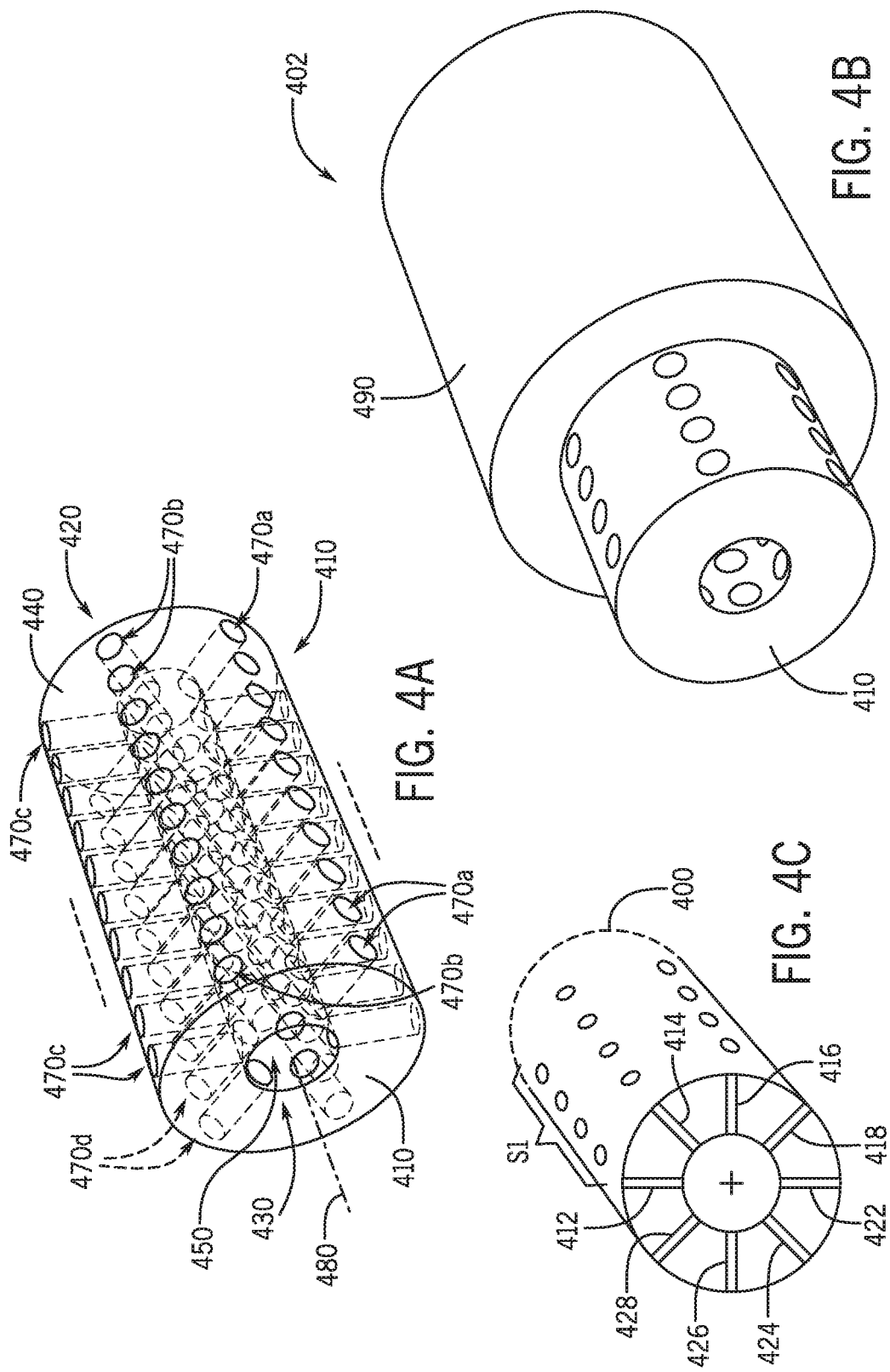

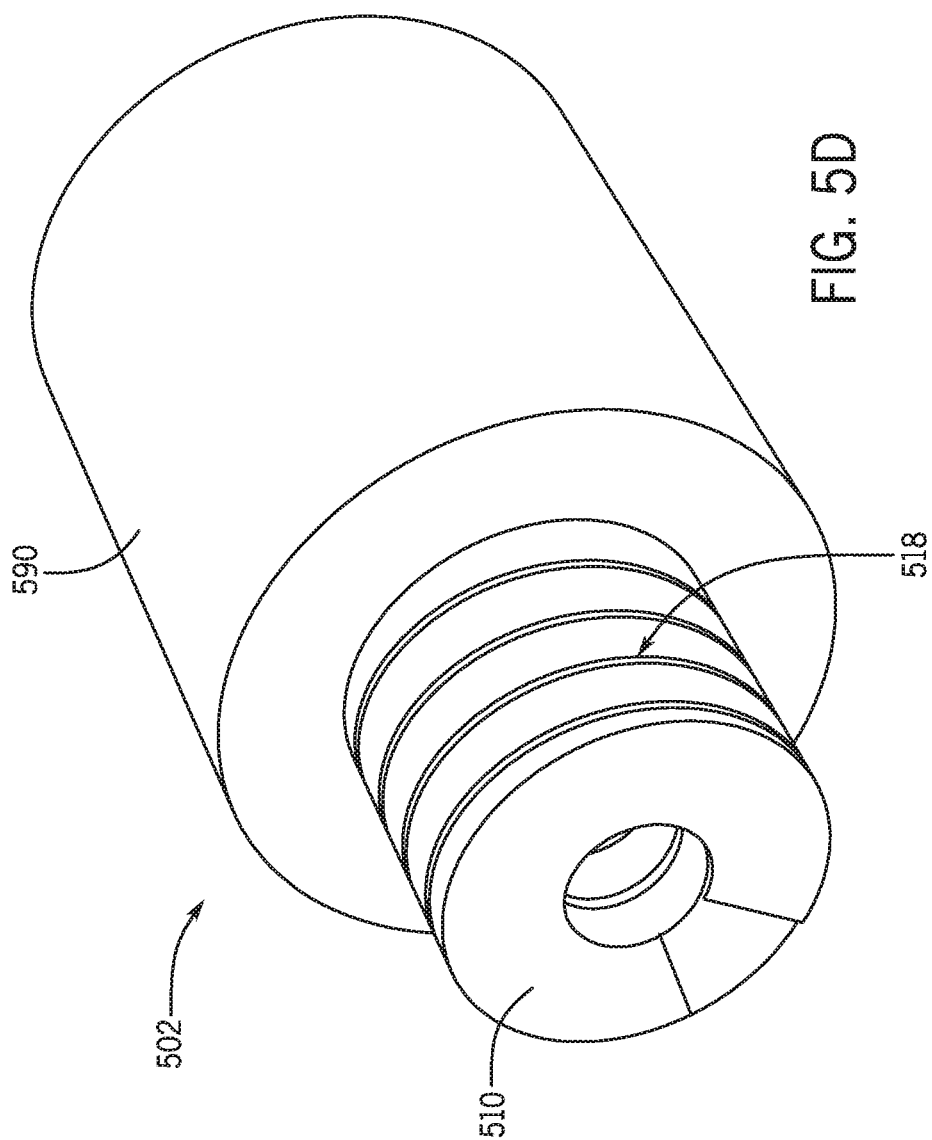

BI-FUNCTIONAL FILTER DEVICE FOR A GAS SAMPLING LINE AND SYSTEM

CROSS-REFERENCE TO RELATED APPLICATION

This application claims priority to and the benefit of U.S. Provisional Application No. 62/583,583, entitled "BI-FUNCTIONAL FILTER DEVICE FOR A GAS SAMPLING LINE AND SYSTEM," filed Nov. 11, 2017, the content of which is incorporated herein by reference in its entirety for all purposes.

FIELD OF THE INVENTION

The present invention generally relates to gas sampling lines for transferring gas samples (e.g., air with a high level of $CO_2$ concentration that is exhaled by a subject) to gas analyzers (e.g., capnograph), and more specifically to a filter and dehumidifier, and to a gas sampling line that includes the filter and dehumidifier for protecting gas analyzers from being clogged or even damaged by liquids (e.g., water condensate or droplets) during operation.

BACKGROUND

A human respiratory cycle includes a sequence of events during which a subject inhales and exhales a given volume of air through the respiratory system. Inlet/outlet gas user interface, for example cannula tubing, face (respiration) masks, tubing adaptors, airways adaptors, and the like, used by subjects suffering from breathing problems typically include an oxygen port for delivering oxygen to them via an oxygen tube, and a $CO_2$ port for drawing $CO_2$ samples of $CO_2$ exhaled by the subject via a $CO_2$ tube. Oftentimes, a subject connected (via a gas sampling line) to a capnograph exhales gases (e.g., mainly $CO_2$, some air, etc.) at the body's temperature, usually about 37 degrees Celsius, and exhaled gases usually have relative humidity which is above 90 percent (typically about 95 percent). During $CO_2$ monitoring, the exhaled gases are drawn by the capnograph along with $CO_2$ samples of the $CO_2$ that the subject exhales. Since the environmental temperature is usually below 37 degrees Celsius, water vapors in the exhaled gases condense in the tubing system as they move along a sampling tube, towards the capnograph. During water vapor condensation, a portion of the water vapor changes phase into liquid water while another portion of the vapors keep the gases in the tube humidified, though less humidified. However, water condensate may reach the capnograph, causing it to clog and, eventually, to malfunction. To mitigate water condensates from reaching the capnograph, capnographs may include a dehumidifier and a filter.

Certain existing filters include a plurality of hollow fibers that are glued at one end of a polyvinyl chloride ("PVC") tube. This type of filter has a rather complex structure that makes automatic production a challenge. In this type of filter, the hollow fibers have to be kinked (in order to make them more efficient), and they are glued among themselves at a specific distance from the kinking. The hollow fibers are then inserted into a PVC filter housing tube, and the 'glued' end of the filter is glued to the tube. The glue layer is sized such that it blocks penetration of liquid (e.g., water) through it. Due to this filter structure, the filters are manufactured manually, which affects production efficiency. In addition, using hollow fibers with submicron holes results in a pressure drop (up to 12 millibar (mbar) at 50 milliliters/minute (ml/min) air flow rate), comparing to a few millibars in a gas sampling tube having the same length and inner diameter. That is, the pressure drop in a filter length unit of certain filters is about 4-5 times greater than the pressure drop in a sampling tube having the same length and inner diameter. The pressure drop problem is exacerbated as water condensate starts to accumulate in the filter. In addition, due to water condensate accumulation in the filter, which changes its pressure drop during operation, the rate at which gas (a mixture of air and carbon dioxide ($CO_2$)) flows into the capnograph changes as well. Changes in the gas ($CO_2$) flow rate may result in unsteady and/or inaccurate $CO_2$ measurements. To solve this problem, the gas flow rate has to be adjusted. In addition, the complex structure is not streamlined; that is, the flow of gas (e.g., $CO_2$) through the filter is not 'smooth' (the gas flow includes vortexes), which results in increased rise time of the measured parameter ($CO_2$ concentration in case of capnography). In addition, a filter having the above-described structure has a rather limited water-capturing and evacuation capacity, which restricts the operation time of the filter (e.g., it gets clogged up), hence the operation time of the $CO_2$ sampling line.

Some gas sampling lines (for example a $CO_2$ sampling line) may also include a separate gas dryer (dehumidifier) in order to dry gas samples as much as possible before the gas samples reach the filter. Adding both the filter and the gas dryer to a gas sampling line is costly, requires an additional manufacturing process, and, in general, more complicated to handle.

While sampling a gas (e.g., $CO_2$) by using a gas sampling line is beneficial, there are undesirable effects associated with the hollow fibers of certain existing filters. It has been recognized that it may be advantageous to have a filter which is capable of both absorbing liquids at a same or, preferably, at a higher rate than is done by certain existing filters and evaporating at least part of the accumulated liquids (e.g., water) without increasing the pressure drop in the filter. Moreover, a filter that both absorbs and evaporates liquids without increasing the pressure drip may facilitate continuous, reliable and accurate measurement and analysis of the sampled gas, and streamlining the flow of the gas samples in the related gas sampling line. It may also be advantageous to have a single device that can function both as a filter and a dehumidifier.

SUMMARY

A bi-functional filter device is designed to function as a filter (to absorb or remove vapor and water condensate from within a sampling tube through which humidified gases flow), and as a dehumidifier (to dehumidify the filter, hence the sampling tube). The bi-functional filter device includes a filter body that includes an axial through-channel that lengthwise passes through the filter's body, through which gas (e.g., humid gas) to be sampled can flow (e.g., to a gas receiving system; e.g., gas monitor, gas analyzer, etc.). The bi-functional filter device also includes a through capillary path in the filter's body that may absorb liquids, for example laterally, radially, or spirally from the through-channel of the filter's body using capillary action, to thus clear the through-channel of the filter's body from these liquids.

In one embodiment, the through capillary path in the filter's body includes, or is, a plurality of through capillary channels in the filter's body that may absorb liquids from the through-channel of the filter's body. The plurality of through capillary channels provide fluid flow communication, or fluid flow path, between the interior space of, or making up, the through-channel to a space external to the filter body; that is, outside the filter body. The capillary channels may be laterally, or radially, disposed along the length of the body and around (e.g., circumferentially with respect to) the through-channel, and function as a filter. The filter body may be made of or include a liquid absorbing material that is capable of absorbing liquid(s) from humid gas(es) flowing in the through-channel of the filter body. The bi-functional filter device also includes a filter sleeve (an evaporating sleeve). The filter sleeve may fully or partly enclose or house the filter body and it is made of or includes a liquid evaporating material capable of evaporating liquid(s) that are absorbed by the filter body. (The terms 'filter sleeve', 'sleeve', 'dehumidifier sleeve' and 'dehumidifier' are used herein interchangeably to mean the same thing.)

In another embodiment, the through capillary path in the filter's body is one, continuous, helically shaped channel. In this embodiment, the filter body is made of, or includes, a helically coiled flat strip having a thickness T and a width Wd. The helically coiled flat strip forms a helicoidal strip structure ("HSS") that includes multiple contiguous helical coil turns (helical 'loops'). In an aspect of this embodiment, the HSS has a uniform internal diameter that defines the filter body's axial through-channel, a uniform external diameter, and a uniform helical spacing that is defined by (e.g., 'runs' between), or is between, the helical coil turns of the HSS. Adjacent helical coil turns of the HSS are flatly and lengthwise retained in close proximity to one another in a way that a small gap that exists between them. The small gap defines the helical spacing and facilitates or enables capillary effect, hence the name "helical capillary channel."

In another aspect of this embodiment (helically coiled flat strip), the HSS has a non-uniform internal diameter defining the filter body's axial through-channel, and/or a non-uniform external diameter, and/or a non-uniform helical spacing that is defined by, or is between, the flat helical coil turns of the HSS. For example, the internal diameter defining the filter body's through-channel and/or the external diameter of the filter body may change non-uniformly (for example linearly or otherwise). Using a filter body through-channel having a non-uniform diameter or using a filter body having a non-uniform external diameter may enhance the filter's capability to separate liquid from gas by virtue of vortex flow. If both diameters are non-uniform, this would increase the rate at which liquid is removed from the filter's through-channel.

While a filter body including, or having therein, a uniform helical spacing may be useful in filtering one type of liquid (e.g., water), a filter body including, or having therein, a non-uniform helical spacing may be useful in filtering more than one type of liquid, for example two types of liquid (e.g., water, saline, medication, or any other liquid). The helical spacing is also referred to herein as 'helical capillary channel' because the helical spacing is designed to effectuate the capillary action. Since the width (gap) of the helical spacing or gap between adjacent coil turns of the HSS is a main factor in determining the capillary properties of the capillary channel, hence of the filter body, changing it along the spiraling direction of the helical capillary channel may facilitate filtering (e.g., by absorbing) more than one type of liquid.

The helical capillary channel (e.g., the spiraling gap or path between adjacent coil turns of the HSS) includes contiguous helical capillary turns, where each helical capillary turn is a 360-degree turn of the helical spacing. The filter body may include N helical capillary turns (e.g., C1, C2, . . . , CN). In some embodiments, the lengthwise density of the helical capillary turns, measured in number of helical capillary turns per length of unit, may be fixed along the filter's longitudinal axis, or it may vary, and it may depend on a desired capillary action and the filter's overall performance in general.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding, or analogous elements. Of the accompanying figures:

FIG. 3A is a cross sectional view of a filter body which is an internal part of a bi-functional filter device for a gas sampling line, in accordance with an embodiment of the present disclosure;

FIG. 3B is a cross sectional view of the filter body of FIG. 3A enclosed or housed by a sleeve-like housing, in accordance with an embodiment of the present disclosure;

FIG. 4A is a perspective view of the filter body of FIG. 3A, in accordance with an embodiment of the present disclosure;

FIG. 4B is a perspective view of the bi-functional filter device of FIG. 3B, in accordance with an embodiment of the present disclosure;

FIG. 4C is a diagram of a filter body including an example number of sets of parallel capillary channels, in accordance with an embodiment of the present disclosure;

FIG. 5D is a perspective view of the bi-functional filter device of FIG. 5C, in accordance with an embodiment of the present disclosure.

DETAILED DESCRIPTION OF THE INVENTION

The description that follows provides various details of exemplary embodiments. However, this description is not intended to limit the scope of the claims but instead to explain various principles of the invention and the manner of practicing it.

The present invention discloses a single, bi-functional, device that functions both as a filter and a dehumidifier. The term "liquid absorption material", as used herein, refers to any material that can absorb a liquid. The term "liquid evaporating material", as used herein, refers to any material that can evaporate a liquid in a direction that is compliant with a humidity gradient in a space containing the liquid evaporating material. The liquid absorbed by the liquid evaporating material evaporates towards, or into, a less humid space, and the rate of the evaporation depends, among other things, on the humidity gradient in the space containing the evaporating material; the greater the humidity gradient, the greater the evaporation rate.

In some embodiments of the present invention, a bi-functional filter device is provided or adapted for a gas sampling line. The bi-functional filter device may include a filter body and a dehumidifier that is formed as a filter sleeve that encloses or houses the filter body. The filter body may include a through-channel that may pass lengthwise through the filter body (e.g., along a longitudinal axis of the filter body). In addition, the filter body may include a through capillary path that, in one embodiment, includes a plurality of separate through capillary channels. In another embodiment, the filter body may include a lengthwise helical capillary channel that includes N contiguous helical capillary turns. The through capillary path provides one or more liquid flow paths from the space of or in the through-channel to a space external to the filter body, hence use of the term "through" in conjunction with "capillary path". The filter body may be or include a liquid absorbing material, and the dehumidifier sleeve may include a liquid evaporating/vaporizing material.

In some embodiments of the present disclosure there is provided a gas sampling line that includes a tube for transferring gas samples from a gas source (e.g., a patient exhaling air, $CO_2$ source, a system outputting gas, etc.) to a gas receiving system (e.g., gas analyzer or monitor), and the bi-functional filter device, where the bi-functional filter device is coupled to the tube and in fluid communication with the tube to form a continuous, fluid flow path. Various example embodiments of a bi-functional filter device are described below.

Figure 1A:
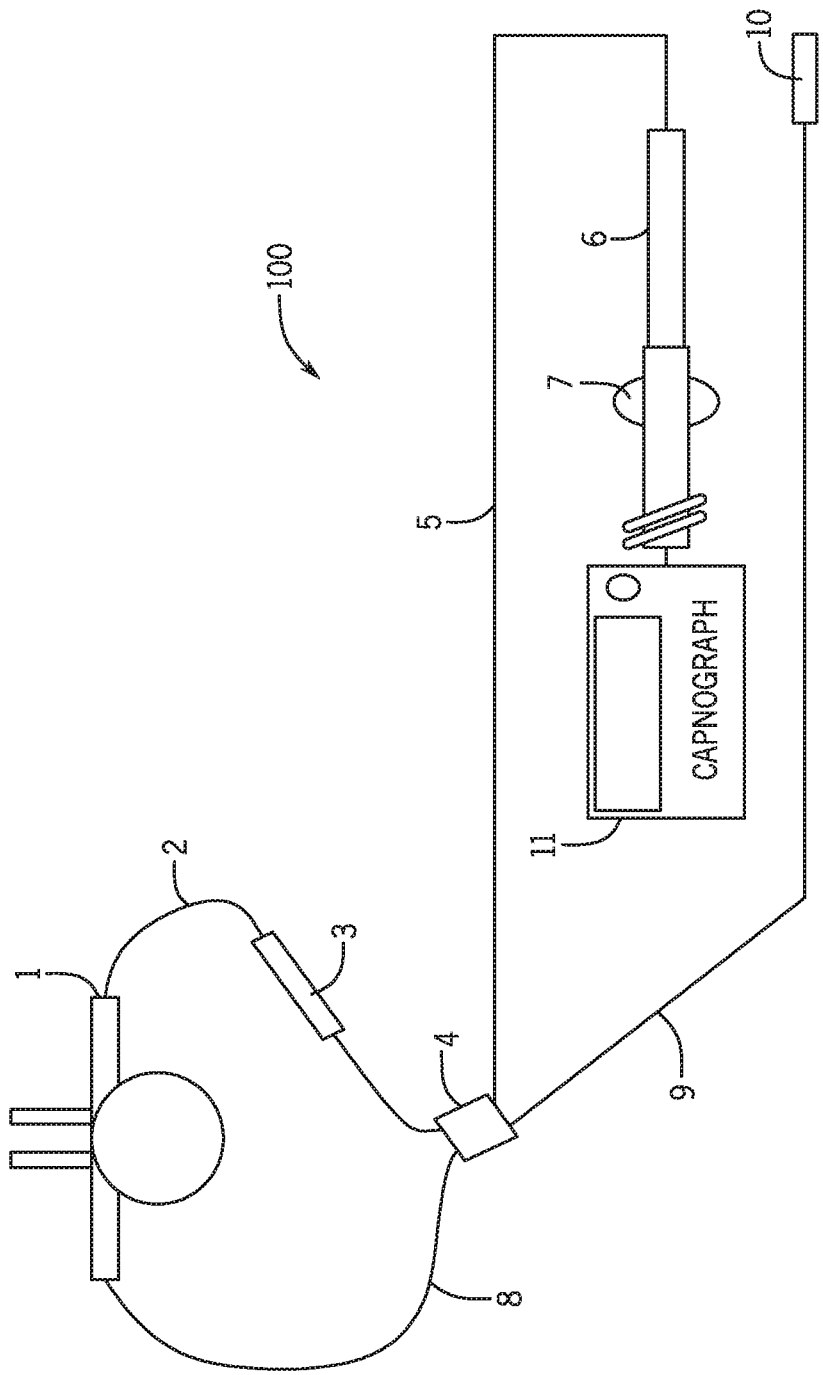
FIG. 1A is a schematic of gas sampling and analyzing system that includes a $CO_2$ monitoring system setup, in accordance with an embodiment of the present disclosure.

Referring to FIG. 1A, an example $CO_2$ monitoring system setup 100, which is an example gas sampling and analyzing system that may be used in conjunction with the bi-functional filter device disclosed herein. The $CO_2$ monitoring system setup 100 includes a cannula 1, a first soft PVC tube 2, dehumidifier 3 (e.g., a Nafion™ dryer), an oxygen-$CO_2$ tube connector 4, a second soft PVC tube 5, a filter assembly 6 for quick seal, a quick seal 7, a third soft PVC tube 8, $O_2$ tube 9, universal connector subassembly 10), and a capnograph 11.

A shown in FIG. 1A, $CO_2$ monitoring system setup 100 uses a device (e.g., the filter assembly 6) that filters and traps liquids, and a separate device (e.g., the dehumidifier 3) that dehumidifies the gas samples before they reach the filter assembly 6. In the illustrated embodiment, the dehumidifier 3 is positioned near the cannula 1, which directs samples of the humid gasses into a sampling tube, and the filter assembly 6 is positioned at an input of the capnograph 11. The filter assembly 6 protects the capnograph 11 from liquids that may pass the dehumidifier 3. This arrangement, of the filter assembly 6 and the dehumidifier 3, provides some protection to the capnograph 11. However, as described above water condensates may flow into the capnograph. In this arrangement, the dehumidifier 3 and the filter assembly 6 are disposed in the $CO_2$ tubing (e.g., the tubes 2, 5). The tubes 8 and 9, which transfer oxygen to the patient, generally do not include a filter assembly and a dehumidifier because, for example, the properties (e.g., flow rate, pressure, humidity, etc.) of the oxygen delivered to the patient are controlled by the system delivering it.

Figure 1B:
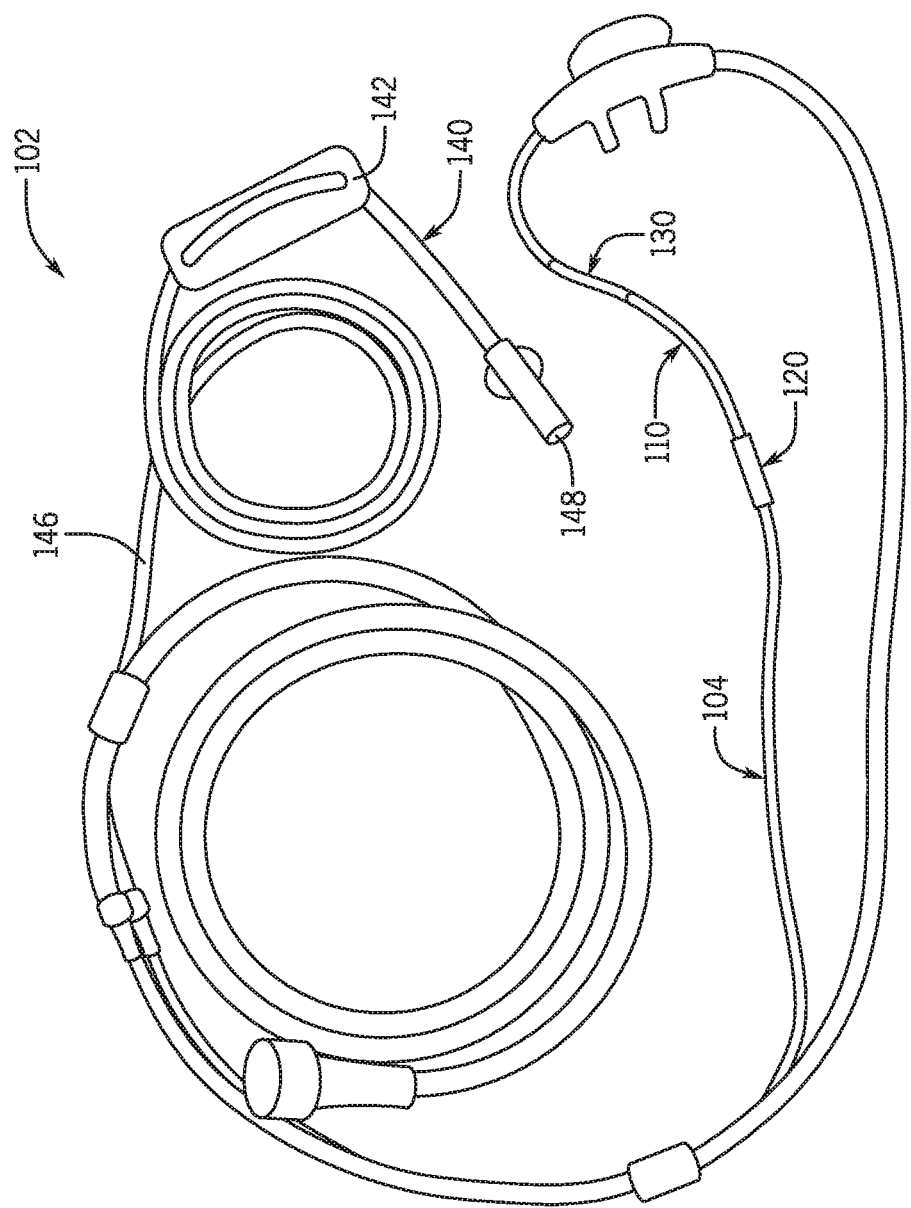
FIG. 1B illustrates a $CO_2$ cannula filter line for sampling $CO_2$ and for delivering oxygen to a subject that may be used with the $CO_2$ monitoring system of FIG. 1A, in accordance with an embodiment of the present disclosure.

FIG. 1B illustrates a $CO_2$ cannula setup 102 for sampling $CO_2$ and for delivering oxygen to a patient that may be used in conjunction with the bi-functional filter device disclosed herein. A cannula tube 104 of cannula setup 102 is connected to a dehumidifier 110 via barb connectors 120 and 130. A filter 140 is located at an end 142 of a $CO_2$ tube 146 of the cannula tube 104, and includes a connector 148 connectable to capnograph 11.

Figure 2A:
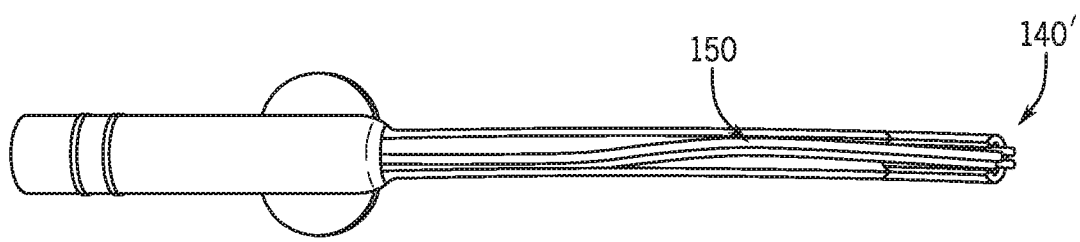
FIG. 2A illustrates a 'kinking' type filter in a tube housing that may be used with the $CO_2$ monitoring system of FIG. 1A.
Figure 2B:
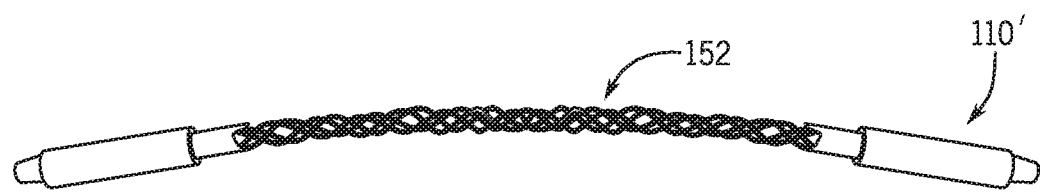
FIG. 2B illustrates a dehumidifier that may be used with the $CO_2$ monitoring system of FIG. 1A.

FIG. 2A illustrates an embodiment of a filter 140' similar to the filter 140 of FIG. 1B. The filter 140' includes a 'kinking' type filter element 150. FIG. 2B depicts a dehumidifier 110' similar to the dehumidifier 110 of FIG. 1B. The dehumidifier 110' includes a dehumidifier element 152 behind a mesh. The dehumidifier element 152 removes moisture that may present in the patient's exhaled breath upstream of the capnograph (e.g., the capnograph 11).

Figure 2C:
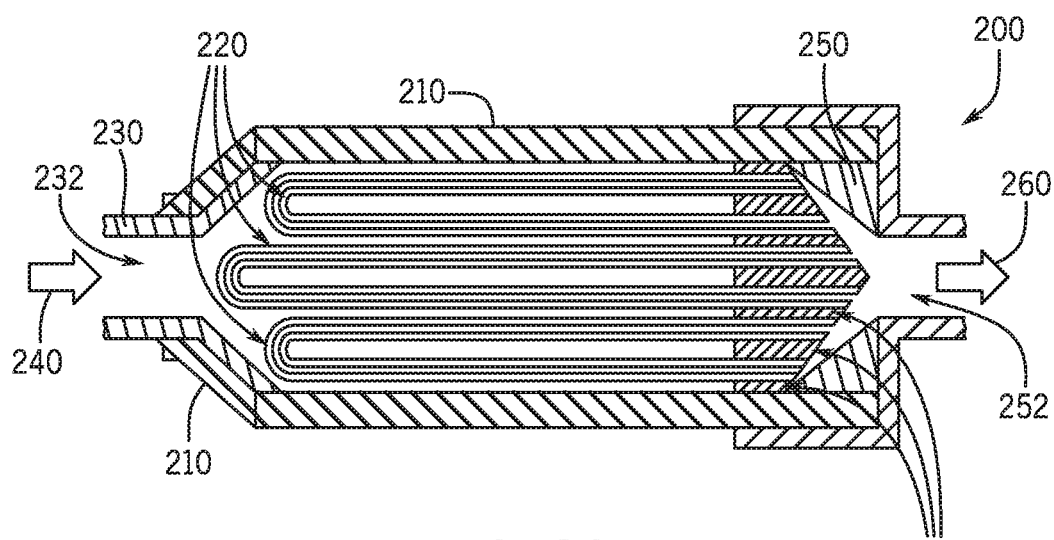
FIG. 2C is a cross sectional view of the 'kinking' type filter of FIG. 2A.

FIG. 2C is a cross sectional view of a filter 200. The filter 200 includes a PVC filter housing tube 210 and multiple hollow fibers 220 that are contained in the PVC filter housing tube 210. Each hollow fiber 220 is permeable to gases but not to liquids. The liquids entering the filter 200 accumulate inside the PVC filter housing tube 210 (e.g., in a space between the hollow fibers 220 and the PVC filter housing tube 210), which may clog the hollow fibers 220. The filter 200 also includes a tapered inlet connector 230 that includes an inlet opening 232 through which humid gas and water condensate 240 enter the filter 200. The filter 200 also includes a tapered outlet connector 250 that includes an outlet opening 252 through which gas 260 exits the filter 200 without liquid or with liquid in vapor phase. The filter 200 also includes a liquid barrier 270 that allows neither gases nor liquids to pass through, towards the outlet opening 252 and out of the filter 200. The liquid barrier 270 may be a layer of glue which is impermeable to gases and liquids. The liquid barrier 270 may also be a mounting basis for multiple hollow fibers 220. The hollow fibers 220 may be mounted (e.g., glued) into the liquid barrier 270 such that each individual hollow fiber jointly forms with the liquid barrier 270 a liquid-free space.

Certain arrangements of filters used in $CO_2$ monitoring may be complex and include many parts that have to be assembled. Due, in part, to the structural complexity of these filters, the parts are assembled manually. In addition, certain existing filters are unidirectional, meaning that gas flows in the filter in one direction (e.g., in a direction toward the capnograph).

FIG. 3A is a cross sectional view of an internal part of a filter body 310 of a bi-functional filter that may be used with a gas sampling line of a $CO_2$ monitoring system (e.g., the $CO_2$ monitoring system setup 100) according to an embodiment of the present disclosure. The filter body 310 of the bi-functional device has a longitudinal length L, a first end 320, and a second end 330. Extending along the longitudinal length L between the ends 320, 330, the filter body 310 includes an external surface 340 and an inner wall 350. The inner wall 350 defines a through-channel 360 that passes through the filter body 310, along its longitudinal length L, from the first end 320 to the second end 330 of the filter body 310. The filter body 310 includes a through capillary path that includes a plurality of capillary channels 370 to draw liquids that may be present in the fluid flowing through a cannula (e.g., the cannula 104) associated with the $CO_2$ monitoring system. The capillary channels 370 may be arranged lengthwise within the filter body 310 along the longitudinal length L of filter body 310 and extend radially (e.g., orthogonal) to the longitudinal length L around the through-channel 360. That is, each capillary channel of the plurality of capillary channels 370 may be stacked in series on top of an adjacent capillary channel along the longitudinal length L between the external surface 340 of filter body 310 and the inner wall 350 of filter body 310 in a manner that the plurality of capillary channels 370 circumferentially surround the through-channel 360. Each capillary channel of the plurality of capillary channels 370 provides a through liquid flow path in the filter body 310 that is crosswise to a flow path through the through-channel 360, from the interior space of the through-channel 360 to a space external to the filter body 310. Liquid may flow in the plurality of capillary channels 370 by means of their capillarity; that is, by using capillary action.

Each capillary channel of the plurality of capillary channels 370 may spatially extend laterally or radially from through-channel 360. In addition, each capillary channel of the plurality of capillary channels 370 may outwardly extend through the filter body 310 from the inner wall 350 towards and through the external surface 340, at an acute angle $\alpha$ (e.g., at an angle of 90±45 degrees) with respect to a longitudinal axis 380 of the filter body 310 (and of the through-channel 360). In certain embodiments, the acute angle $\alpha$ is 90 degrees in order to remove liquids from the through-channel 360 as quickly as possible, using the shortest path possible.

The filter body 310 may be made of or include hydrophilic material and/or a liquid absorbing material. Using the hydrophilic material may make the filter body 310 impermeable to gases, and, in addition, the hydrophilic material may be selected so as to facilitate an even distribution of liquids across its surface, thereby increasing the capillary effect. The liquid absorbing material may be made of or include materials such as sulfonated tetrafluoroethylene based fluoropolymer-copolymers, polyether block amide (PEBA) and/or any other suitable plastic material that is capable of absorbing a liquid and combinations thereof. By way of non-limiting example, the liquid absorbing material may be Nafion™ and/or Flemion™ and/or Pebax® and/or AP-102.

The filter body 310 may be bi-directional; that is, a gas (humid or not) may flow from the first end 320 of the filter body 310 to the second end 330 of the filter body 310 (that is, in a direction 305) or vice versa (e.g., in the opposite direction). Both gas flow directions may result in a same or similar gas filtration efficacy. The filter body 310 may be symmetrical (e.g., structurally and/or functionally) with respect to a flow direction of a humid gas flowing in the through-channel 360.

The filtration properties (absorbing liquids) of the filter body 310 is implemented by the plurality of capillary channels 370 and by manufacturing the filter body 310 from a material that is capable of absorbing liquids. That is, the filter body 310 may absorb liquids through, or by using, the plurality of capillary channels 370, and by a liquid(s) absorbing material that the filter body 310 is made of or includes. The filter body 310 may entirely be made from liquid(s) absorbing material(s), or only part of the filter body 310 may be made from such materials.

FIG. 3B is a bi-functional filter device 302 that includes the filter body 310 of FIG. 3A. Additionally, the bi-functional filter device 302 includes a filter sleeve 390 that may dehumidify fluids flowing through the bi-functional filter device 302. Accordingly, the filter sleeve 390 may be referred to as a dehumidifier sleeve. The filter sleeve 390 (e.g., dehumidifier) is an evaporation sleeve, layer, or coating that is external to and air-tightly encloses or houses the filter body 310. The filter sleeve 390 may be made of or include hydrophilic material(s) and a liquid evaporating material. The liquid evaporating material may include materials such as sulfonated tetrafluoroethylene based fluoropolymer-copolymers, polyether block amide (PEBA) and/or any other suitable plastic material that is capable of absorbing and/or evaporating a liquid and combinations thereof. By way of non-limiting example, the liquid absorbing material may be Nafion™, Pebax®, and/or AP-102.

In certain embodiments, the liquid absorbed by the liquid absorbing material and, depending on the embodiment, evaporated by the evaporating sleeve is water. However, the liquid absorbing material and liquid evaporating material may also absorb, transfer, and evaporate other liquids in addition to or instead of water. For example, the liquid absorbing material and the liquid evaporating material may absorb, transfer, and evaporate the liquid absorbed. In some embodiments, the liquid absorbing material may be selected according to the liquid to be filtered out (e.g., removed from the through-channel 360). If more than one type of liquid is to be removed from the through-channel 360, the liquid absorbing material may include a liquid absorbing material for each type of liquid, or for several liquids.

The filter body and/or the filter sleeve may include a material whose color changes according to an amount of liquid that is absorbed by the liquid absorbing material. Such materials are generally called "chromatic adsorbents". For example, some silica gels change their color (e.g., from blue to pink, from orange to black) during water adsorption, or when exposed to humidity.

The color change may be correlated to, or be an indication of, an operational time and/or state of the filter device. For example, the color change may be correlated to, or be an indication of, an operational time and/or state of the liquid absorbing material of the filter body. By way of non-limiting example, the color, or a change in the color, may indicate when the liquid absorbing material is saturated with the absorbed liquid. That is, the absorbing material has absorbed an amount of liquid (e.g., water) that impairs the capability of the liquid absorbing material to further absorb liquids.

The filter body 310 and the filter sleeve 390 may structurally be concentric. The filter body 310 and the filter sleeve 390 may have a shape that is rounded, for example circular. For example, the filter body 310 and the filter sleeve 390 may be cylindrical. In certain embodiments, an inner diameter, D1, of the filter body 310 may be 1±0.5 millimeters, and an outer diameter, D2, of the filter body 310 may be 3±1 millimeters. Additionally, an outer diameter, D3, of the filter sleeve 390 may be 5±2 millimeters. The filter body 310 and the filter sleeve 390 may be made of, or include, a PVC material. However, any other suitable polymer may be used to manufacture the filter body 310 and the filter sleeve 390.

FIG. 4A is a three-dimensional view of a filter body 410 of a bi-functional filter device according to an embodiment of the present disclosure. In the illustrated embodiment, the filter body 410 is cylindrical. However, the filter body 410 may have any other suitable shape. The filter body 410 may have a longitudinal axis 480, and include a first end 420, a second end 430. An external surface 440 and an inner wall 450 that defines a through-channel extends between the ends 420, 430 along the longitudinal axis 480. The through-channel passes all the way through the filter body 410 from first end 420 to second end 430 of filter body 410. The filter body 410 also includes a through capillary path that includes a plurality of capillary channels 470 to draw liquids from the through-channel via capillary action (capillary motion). The plurality of capillary channels 470 may be radially and lengthwise disposed in the filter body 410 and around the through-channel, between the external surface 440 and the inner wall 450 of the filter body 410. Each capillary channel of the plurality of capillary channels 470 provides a through liquid flow path in the filter body 410, from the interior space of the through-channel to a space external to the filter body 410.

The plurality of capillary channels 470 may spatially extend laterally, or radially, from the through-channel, such that each capillary channel of the plurality of capillary channels 470 may outwardly extend through the filter body 410 from the inner wall 450 towards and through the external surface 440, for example, at an angle $\alpha=90\pm45$ degrees with respect to a longitudinal axis 480 of the filter body 410. By way of example, a first set of parallel capillary channels (e.g., capillary channels 470a) outwardly extends in a first direction, a second set of parallel capillary channels (e.g., capillary channels 470b) outwardly extends in a second direction that is different from the first direction, a third set of parallel capillary channels (e.g., capillary channels 470c) outwardly extends in a third direction that is different from the first and second directions, and a fourth set of parallel capillary channels (e.g., capillary channels 470d) outwardly extends in a fourth direction that is different from the first, second and third directions. The filter body 410 may include a number of sets of the parallel capillary channels which is different than four. For example, the filter body 410 may also include fifth and sixth sets of parallel capillary channels 470. Each set of parallel capillary channels may positioned lengthwise within the filter body 410, parallel to the longitudinal axis 480 of the filter body 410. The filter body 410 may be made of or include hydrophilic material and/or liquid absorbing material.

FIG. 4B is a bi-functional filter device 402 similar or corresponding to bi-functional filter device 302 of FIG. 3B. The bi-functional filter device 402 includes a filter body 400 and a filter sleeve 490 which air-tightly encloses the filter body 410. Part of the filter body 410 is shown outside the filter sleeve 490 (e.g., not enclosed by the filter sleeve 490, for illustration purposes). In practice, the filter body 410 is, or may be, completely lengthwise enclosed by the filter sleeve 490.

The efficacy of the bi-functional filter devices 302, 402 in removing liquid (e.g., by absorbing liquids and evaporating them) from a sampling line incorporating them depends, among other things, on the configuration (e.g., number, size, diameter, etc.) of the capillary channels (or capillary path in general) in the filter body (e.g., the filter bodies 310, 410) and on the amount of liquid that the material(s) of the filter body can absorb. In addition, the efficacy of the bi-functional filter devices 302, 402 may depend on the liquid evaporation rate of the filter sleeve. The greater the number of the capillary channels in the filter body (e.g., as shown in FIGS. 4A-4C), the greater the rate at which liquid(s) can be removed (absorbed) from the through-channel and transferred to the filter sleeve. Also the greater the filter capacity, and the greater the filter sleeve's capability to evaporate liquids transferred from the filter body, the higher the efficacy of the bi-functional filter device. The number of capillary channels that a bi-functional filter device can have may be increased by increasing the size of the filter body (e.g., increasing its length and/or diameter) and lengthwise adding capillary channels, and/or by adding capillary channels to the filter body by increasing the spatial density (angular and/or lengthwise densities) of the capillary channels in the filter's body.

In some embodiments, the filter sleeve (e.g., the filter sleeve 390, 490) may be made of a non-evaporating material (e.g., a material that does not vaporize liquids) that externally seals the filter body (e.g., the filter body 310, 410) to inhibit liquids evaporation through the filter sleeve. If a non-vaporizing material is selected for a filter sleeve, liquid absorbed by or in the filter body cannot be evaporated. Instead, liquid is retained by or in the filter body. At some point, the filter body may no longer be able to absorb more liquid, in which case excessive liquid(s) will start accumulating inside the through-channel of the filter body. As such the filter device would have to be replaced. The material the filter body is made of or includes may be selected to extend the filter device's operation time as much as possible.

The diameter of the capillary channels may be small (e.g., less than 5 millimeters) so that the channels can draw liquids using capillary action. In addition, having a small diameter, the capillary channels may not create vortices, or other interferences, in the gas flow in the through-channel of the filter body. Absent interference from the capillary channels (and absent of other interferences), the physical properties (e.g., flow rate, gas concentration level, pressure ratio, etc.) of the gas that flows through the bi-functional devices (e.g., bi-functional devices 302, 402) are maintained stable in the bi-functional devices. Due, in part, to the design of the bi-functional filter device, gas can flow in the filter device with minimal to non-existent interference.)

FIG. 4C illustrates a filter body 400 including a capillary path that, by way of example, includes eight sets (sets S1, S2, . . . , S8) of parallel capillary channels according to an embodiment of the present disclosure. Only one set of parallel capillary channels is referred to in FIG. 4C; namely, set S1. The capillary channel 412 is one (e.g., a first) capillary channel of the first set, S1, of the parallel capillary channels; a capillary channel 414 is one (e.g., a first) capillary channel of a second set, S2, of the parallel capillary channels; a capillary channel 416 is one (e.g., a first) capillary channel of the third set, S3, of the parallel capillary channels; a capillary channel 418 is one (e.g., a first) capillary channel of the fourth set, S4, of the parallel capillary channels; a capillary channel 422 is one (e.g., a first) capillary channel of the fifth set, S5, of the parallel capillary channels; a capillary channel 424 is one (e.g., a first) capillary channel of a sixth set, S6, of the parallel capillary channels; a capillary channel 426 is one (e.g., a first) capillary channel of the seventh set, S7, of the parallel capillary channels, and a capillary channel 428 is one (e.g., a first) capillary channel of the eighth set, S8, of the parallel capillary channels. The capillary channels in a set need not be parallel.

The sets of parallel capillary channels can be arranged angularly around the longitudinal axis of the filter body according to a need, for example according to the type of liquid to be absorbed and evaporated and/or according to the gas flow rate. In the embodiment illustrated in FIG. 4C there are eight sets of capillary channels. By way of example, in FIG. 4C the angle between each set, Si, of the capillary channels and a subsequent set, Si+1, of the capillary channels is 45 degrees (360°/8). Sets of the capillary channels may angularly be spaced apart by using other angles. Referring again to FIGS. 3A-3B and also to FIGS. 4A-4C, the density of the capillary channels may change longitudinally (e.g., using different numbers of capillary channels per unit of length) or angularly (e.g., using different numbers of sets of capillary channels, or different number of capillary channels per unit of angle), or both longitudinally and angularly, with respect to the filter body longitudinal axis (e.g., the axis 380 of the filter body 310). The density of the capillary channels and/or the diameter of the capillary channels may be selected (e.g., they may be optimized) according to the liquid to be absorbed and evaporated from the through-channel. Some capillary channels may have a different diameter than other capillary channels to enable the filter device to efficiently remove (e.g., by absorbing and vaporizing) different types of liquids from the through-channel. (The diameter, or diameters, of capillary channels may be selected, for example, so as to optimize removal of specific, or target, liquid or liquids.) The density of the capillary channels may be irregular with respect to the filter body's longitudinal axis in order to define different filtration rates, for example, with respect to the direction at which humid gas flows in the through-channel of the filter body.

The filter body and/or the filter sleeve may include a material that changes color according to the amount of liquid that is absorbed by the filter body. The color of the material may be correlated to and/or indicative of an operational time and/or state of the liquid absorption material of the filter body, or an operational time and/or state of the liquid evaporation material of the filter sleeve.

Figure 5A:
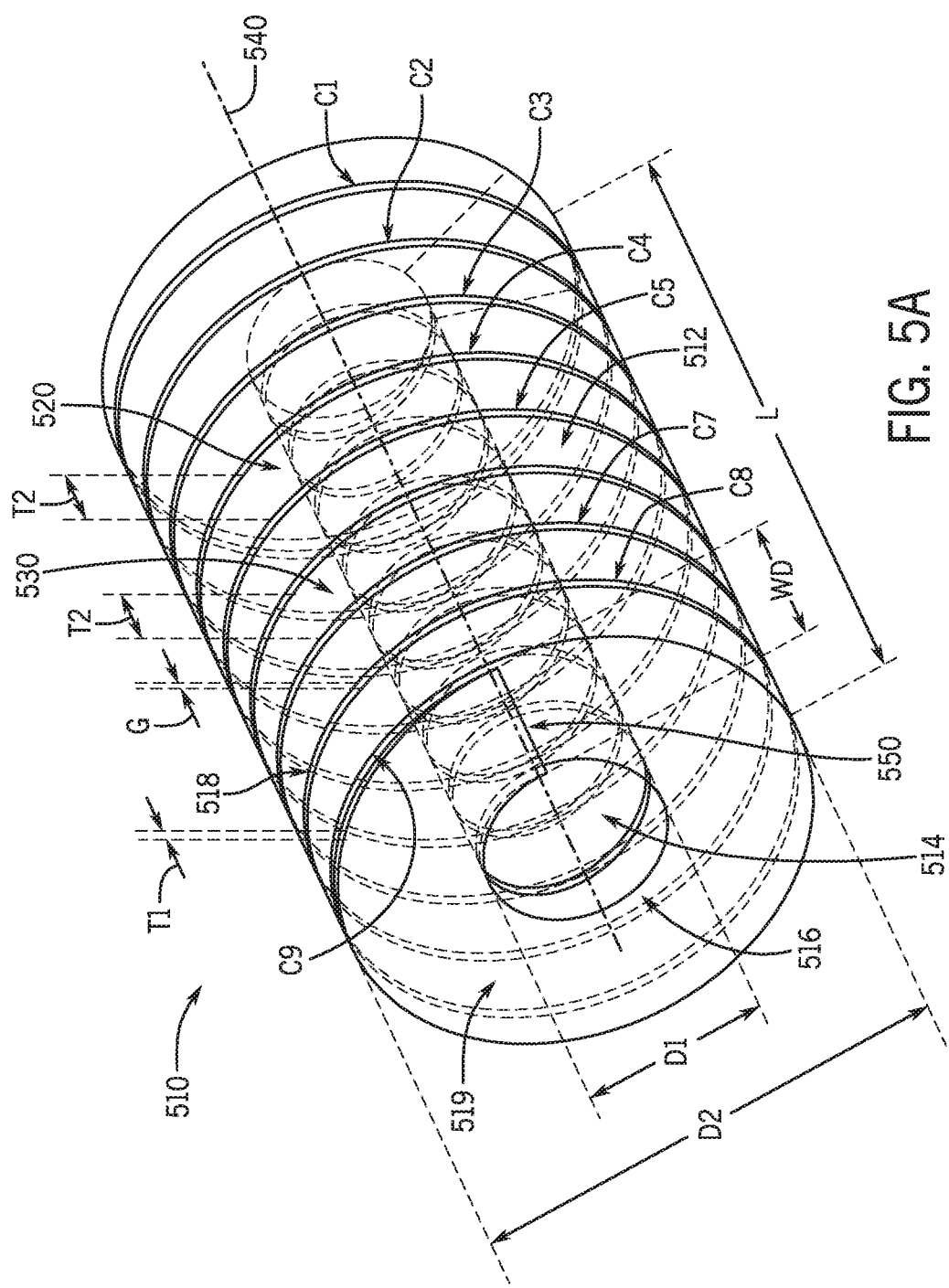
FIG. 5A is a perspective view of a filter body which is an internal part of a bi-functional filter device for a gas sampling line, in accordance with an embodiment of the present disclosure.

While the through capillary channel may include a plurality of separate capillary channels (as demonstrated, for example, by FIG. 4A), the through capillary channel may be one, continuous, helical channel, as demonstrated, for example, by FIG. 5A.

Testing of the filter configuration of FIGS. 3A-3B (and also of FIGS. 4A-4C) indicated that the filter configurations had an extended length of operating time of three hours and thirty minutes, compared to three hours for filters that did not include the disclosed capillary channels. The filter configuration of FIGS. 3A-3B was tested using a longitudinal length L=90 millimeters (mm); D1=1 mm, D2=2.58 mm and D3=3.7 mm, and both the filter body 310 and the filter sleeve 390 were made from a liquid absorption material.

FIG. 5A shows a filter body 510 which is part of a bi-functional filter device for a gas sampling line according to another embodiment of the present disclosure. The filter body 510 has a longitudinal length L and a longitudinal axis 540. The filter body 510 also includes an external surface 512 and an inner wall 514. The inner wall 514 defines a through-channel 516 within the filter body 510 that extends lengthwise through the filter body 510. The filter body 510 also includes a through capillary path in the form of one, continuous, helical capillary channel 518 that provides a spiral shaped liquid flow path from the through-channel 516 to a space external to the filter body 510. The helical capillary channel 518 may absorbs liquids from the through-channel 516 of the filter body 510 by using capillary action.

The filter body 510 includes or is made by helically coiling a flat strip 519 that forms a helicoidal strip structure (HSS) having multiple contiguous helical coil turns. The contiguous helical coil turns are better shown, for example, in FIG. 5B. The helically coiled flat strip 519 forms the through-channel 516 in the filter body 510 and also the helical capillary channel 518 that provides liquid flow path(s) between the external surface 512 and the inner wall 514 of the filter body 510. The helical capillary channel 518 includes a helical spacing (gap "G" in FIG. 5A) between contiguous helical coil turns of the helicoidal strip structure (HSS). That is, the gap "G" is defined by or separates the helical coil turns of the helicoidal strip structure.

The helicoidal strip structure (HSS) obtained by the coiling flat strip 519 may include an inner diameter D1 and an external diameter D2, in a similar way shown, for example, in FIG. 3A. A width "Wd" of the flat strip 519 (Wd=D2−D1) may have a value selected from a range of between approximately 0.1-5.0 millimeters (mm), and the longitudinal length "L" of the filter body 510 (the HSS) may have a value selected from a range of between approximately 1.0-200 mm.

The spiraling gap or spacing making up or defining through the helical capillary channel 518 may include N contiguous helical capillary turns, where each helical capillary turn is a 360-degree turn ('loop') of the helical spacing, separating a respective pair of contiguous helical coil turns of the flat strip 519. Each two, adjacent, helical coil turns of the flat strip 519 are separated by a respective helical capillary turn. Referring to FIG. 5A, the helical capillary channel 518 includes nine contiguous helical capillary turns, designated as C1, C2, . . . , C9 (e.g., N=9)

In some embodiments, the lengthwise density of the N helical capillary turns in the direction of the filter's longitudinal axis, measured as the number of helical capillary turns per length of unit, may be fixed, as shown in FIG. 5A. Alternatively, the lengthwise density of the N helical capillary turns may vary, for example linearly or otherwise; e.g., non-linearly, in direction of the filter's longitudinal axis. Determination of the density of the N helical capillary turns and/or of the number of such turns may depend on a desired capillary action and/or on the filter's overall performance.

In some embodiments, the flat strip 519 may have a uniform thickness, T, along its length, or along most of its length. As used herein, "along most of its length" is intended to denote along the length of the flat strip 519 excluding the two ends, or two end portions of flat strip 519. The thickness T1 shown in FIG. 5A of each end portion of the flat strip 519 may gradually increase (e.g., in one end portion from strip end 550) until the strip's thickness reaches thickness T2, the thickness of the flat strip 519 between the two, opposing, strip ends.

The helically coiled flat strip 519 includes multiple helical turns, two of which are shown at 520 and 530 which, by way of example, have the same thickness T2. The thickness of the helical turns of the helically coiled flat strip 519 may be uniform, at least partly, as described herein, to obtain one filtering effect, or the width of the helical turns of the helically coiled flat strip 519 may vary to obtain other filtering effects.

The following structural parameters of the HSS may affect operation of the filter body 510 in terms of, for example, filtering effect and/or liquid absorption. Moreover, any combination of these parameters may be manipulated to obtain a desired filtering effect, for example, in terms of type, or types, of liquid(s) to be filtered, the rate at which the liquid is absorbed by the filter body 510 (including by the helical capillary channel 518). By way of non-limiting example, the list of parameters may include, among other things, the following parameters:

1. The number of the helical turns of the helically coiled flat strip 519.
2. The lengthwise density of the helical turns of the helically coiled flat strip 519.
3. The length of the spiraling gap or spacing defining the helical capillary channel 518.
4. The number of helical capillary turns, C1, C2, . . . , CN, of the helical capillary channel 518.

5. The lengthwise density of the helical capillary turns C1, C2, ..., CN.
6. The overall length, L, of the filter body 510.
7. The diameters, D1 and D2, of the filter body 510.
8. The thickness, T, of the helical turns of the flat strip 519.
9. The spacing, G, between the helical turns of the flat strip 519.
10. The material(s) the filter body 510 is made of.

Figure 5C:
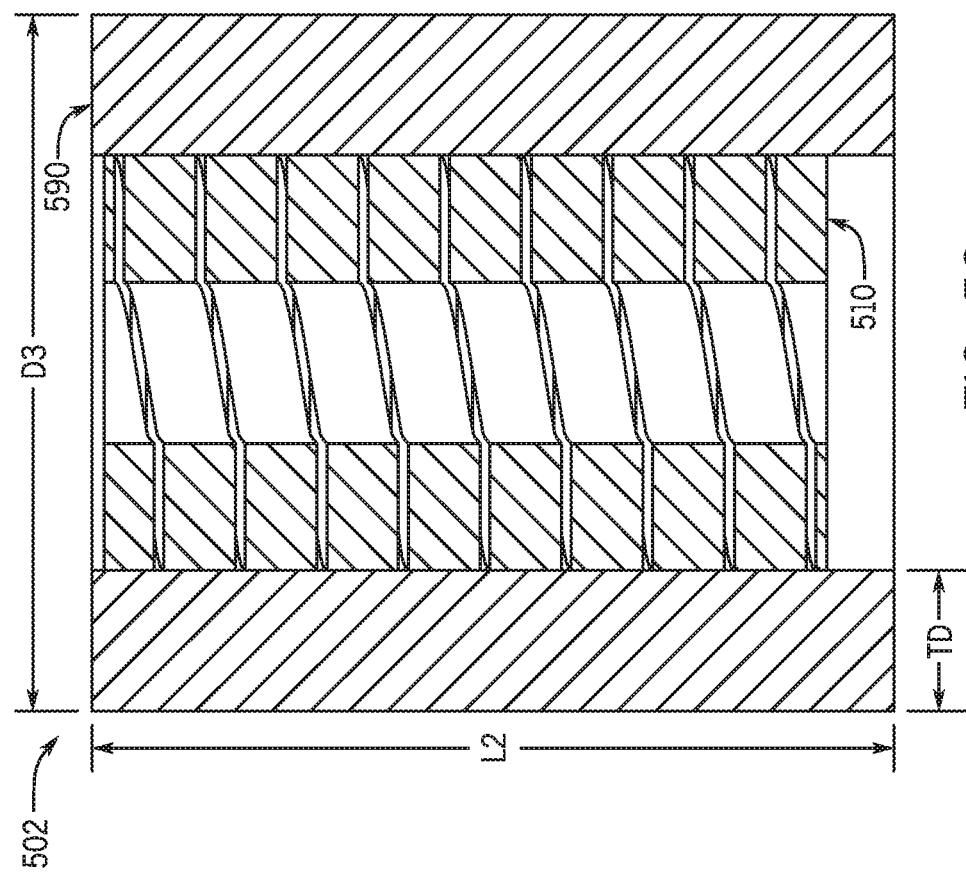
FIG. 5C is a cross sectional view of the filter body of FIG. 5B enclosed or housed by a sleeve-like housing, in accordance with an embodiment of the present disclosure.
Figure 5B:
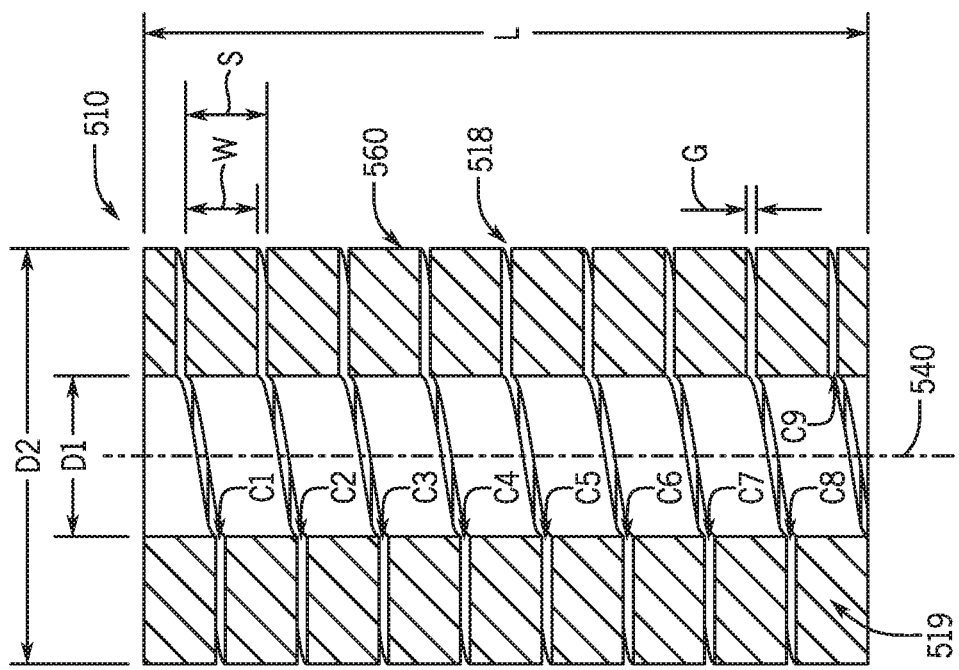
FIG. 5B is a cross sectional view of the filter body of FIG. 5A, in accordance with an embodiment of the present disclosure.

FIG. 5B is a cross sectional view of the filter body 510 of FIG. 5A, which includes, among other things, the helical turn 560 of the helically coiled flat strip 519, and the contiguous helical capillary turns C1, C2, ..., C9 making up or defining through the helical (spiraling) capillary channel 518. FIG. 5B also shows the helical spacing (e.g., the gap G) existing between the helical turns of the helically coiled flat strip 519.

Also shown in FIG. 5B are the thickness, W, of the coil turns of the helically coiled flat strip 519, and a capillary interval (e.g., step), S, defining, for each particular coil turn of the helically coiled flat strip 519, the structural relationship between the particular coil turn and a conjugated space/gap, G; namely, a helical space/gap that is in the same interval as the particular coil turn and that exists between, or defined by, the particular coil turn and a coil turn that is adjacent to the particular coil turn. The adjacent coil turn is part of, or belongs to, an adjacent capillary interval.

The relationship between S, W, and G is defined as $S_i - W_i = G_i$, where $S_i$ is the capillary interval related to a particular coil turn (i) of the helically coiled flat strip 519, $W_i$ is the thickness of the particular coil turn i, and $G_i$ is the spacing/gap i between the particular coil turn i and an adjacent coil turn i+1 or i−1, where the coil turn i+1 follows the particular coil turn in the ordered coil turns, hence it is in a following capillary interval, and the coil turn i−1 precedes the particular coil turn in the ordered coil turns, hence it is in a preceding capillary interval. The number of capillary intervals of or in the helically coiled flat strip 519, and other parameters of the body filter, which are described herein, may be manipulated to obtain a desired filtering effect. The thickness, W shown in FIG.), of the coil turns can be selected, for example, from the range of approximately 0.1-1.0 mm. The smaller the value of W, the better in terms of performance of the filter. Regardless of the value of W selected (e.g., from the range of approximately 0.1-1.0 mm), the capillary interval, S, is larger than W in order to obtain the capillary action.

FIG. 5C is a cross sectional view of a bi-functional filter device 502 including the filter body 510 of FIG. 5B and a dehumidifier 590. The dehumidifier 590 is shaped as a sleeve that is adapted to enclose, or house, the filter body 510. The size, shape, material(s) and functional properties of the dehumidifier 590 may be similar to those of the filter sleeve 390 (e.g., dehumidifier) of FIG. 3B. The description of the sleeve 390 is, or may also be applicable, to the sleeve/dehumidifier 590. The dehumidifier 590 has an internal diameter that is slightly larger than the outer diameter D2 of the filter body 510. As used herein "slightly larger" is intended to denote an outer diameter D2 that is just large enough to enable insertion, at least partially, of the filter body 510 into the dehumidifier 590, which may be regarded as a dehumidifier sleeve. The dehumidifier 590 also has an external diameter D3 that is larger than D2, and a length, L2 that may be identical to the longitudinal length L1 (the length of the filter body 510), or longer than the longitudinal length L1. The length, L2, and thickness, TD, of the dehumidifier sleeve 590 may be manipulated to obtain a desired dehumidification property.

FIG. 5D is a three-dimensional depiction of the bi-functional filter device 502 of FIG. 5C, with the filter device 502 only partly inserted into the dehumidifier (sleeve) 590 for illustration purposes. In FIG. 5C, the filter device 502 is fully inserted (fully housed or enclosed) within the dehumidifier 590.

The bi-functional filter device disclosed herein has many advantages, some of which are described below:

1. The bi-functional filter device has a simple structure (yet it has enhanced efficacy compared to certain existing filters) that facilitates automatic production thereof with reduced manufacturing costs.

2. The bi-functional filter device produces significantly lower pressure drop as gas flows in the through-channel, which is similar to the pressure drop in a PVC tube that has the same inner diameter and length. This advantage may result from the fact that the inner space of the through-channel in the filter's body does not contain any structural gas flow interfering objects. In addition, the through-channel is kept essentially clear of liquids during operation because liquids are continually laterally drawn out from the through-pass channel to the periphery surface of the filter body and evaporated through or by the filter sleeve enclosing the filter body during operation. Due, in part, to its design, the pressure drop caused by the bi-functional filter device does not change during gas sampling operation because liquids are removed laterally, or radially, from the gas flow, thus maintaining the gas flow uninterrupted. In certain existing filters, liquids are accumulated until the filters get clogged. Therefore, the filter may be impermeable to gases, including to the gas being monitored.

3. The gas analysis rise-time provided by the bi-functional filter device is significantly lower than the rise-time caused by certain existing filters.

4. Due, in part, to the capability of the bi-functional filter device to both absorb and evaporate liquids, the filter device disclosed herein can replace two components—the filter and the dehumidifier, which are separated devices in certain existing filters.

5. Due, in part, to the reduced rise-time and lower pressure drop, the bi-functional filter device disclosed herein may have different lengths for different applications. Controlling the length and the internal diameter of the filter body enables designing the filter device for a required operation time.

Although portions of the discussions herein refer to a gas sampling system and to a gas sampling line for sampling and analyzing $CO_2$, the present disclosure is not limited in this regard, and a similar bi-functional filter device may be used in gas sampling lines that may be used to sample or analyze gases other than $CO_2$, and in gas delivering systems. For example, the bi-functional filter device disclosed herein may be used in oxygen sampling systems, in pulmonary function testing system, and in other sampling lines that are related to breathing gas sampling systems. Those skilled in the art of gas sampling will understand how to implement the disclosed filter device in other types of gas analyzers, and will readily appreciate that numerous changes, variations, and modifications, for example only to the filter body (the filter part absorbing liquids) of the bi-functional filter device, or only to the dehumidifying part (the filter sleeve evaporating absorbed liquids), or to both filter body and filter sleeve, can be made without departing from the scope of the present disclosure. Changes, variations, or modifications in the filter body and in the filter sleeve may be made with respect to the materials and/or size (e.g., lengths, diameters) of the filter's body and sleeve, as well as with respect to the capillary channels configuration, setup or layout in the filter's body.

The invention claimed is:

1. A bi-functional filter device for a gas sampling line, comprising:
a filter body having a length and a longitudinal axis, the filter body comprising:
an external surface;
an inner wall defining a through-channel passing lengthwise through the filter body, and
a capillary path passing, and providing a liquid flow path, from the through-channel to a space external to the filter body, wherein the capillary path is configured to absorb liquids from the through-channel of the filter body using capillary action; and
a dehumidifier sleeve enclosing the filter body, the dehumidifier sleeve configured to evaporate liquid absorbed by the filter body.

2. The bi-functional filter device of claim 1, wherein the capillary path comprises a plurality of separate capillary channels disposed in the filter body around the through-channel, between the external surface of the filter body and the inner wall of the filter body.

3. The bi-functional filter device of claim 2, wherein the plurality of separate capillary channels provide the liquid flow path in the filter body from the through-channel to the space external to the filter body.

4. The bi-functional filter device of claim 2, wherein the plurality of separate capillary channels extends laterally or radially from the through-channel of the filter body.

5. The bi-functional filter device of claim 2, wherein the plurality of separate capillary channels outwardly extends through the filter body from the inner wall to the external surface at an angle $\alpha=90\pm45$ degrees with respect to the longitudinal axis of the filter body.

6. The bi-functional filter device of claim 2, wherein a diameter of the plurality of separate capillary channels is selected according to the liquids to be absorbed.

7. The bi-functional filter device of claim 2, wherein a first portion of the plurality of separate capillary channels has a first diameter that is different from a second diameter of a second portion of the plurality of separate capillary channels.

8. The bi-functional filter device of claim 2, wherein a density of the plurality of separate capillary channels changes longitudinally or angularly, or both, with respect to the longitudinal axis of the filter body.

9. The bi-functional filter device of claim 1, wherein the filter body comprises a material selected from the group consisting of a hydrophilic material and a liquid absorbing material.

10. The bi-functional filter device of claim 1, wherein the filter body comprises a material selected from the group consisting of: sulfonated tetrafluoroethylene based fluoropolymer-copolymers, polyether block amide (PEBA), plastic material that is capable of absorbing a liquid, and combinations thereof.

11. The bi-functional filter device of claim 1, wherein the dehumidifier sleeve comprises a material selected from the group consisting of a hydrophilic material and a liquid evaporating material.

12. The bi-functional filter device of claim 1, wherein the dehumidifier sleeve comprises a liquid non-evaporating material.

13. The bi-functional filter device of claim 1, wherein the dehumidifier sleeve comprises a material selected from a group consisting of: sulfonated tetrafluoroethylene based fluoropolymer-copolymers, polyether block amide (PEBA), plastic material that is capable of absorbing a liquid, and combinations thereof.

14. The bi-functional filter device of claim 1, wherein the filter body is configured to absorb the liquid.

15. The bi-functional filter device of claim 1, wherein a material of the filter body is selected according to the liquid to be absorbed.

16. The bi-functional filter device of claim 1, wherein the filter body and/or the dehumidifier sleeve comprises a material that changes color according to an amount of liquid that is absorbed by the filter body.

17. The bi-functional filter device of claim 16, wherein the color, or color change, is correlated to an operational time and/or state of the filter device.

18. The bi-functional filter device of claim 1, wherein the filter body and the dehumidifier sleeve are concentric.

19. The bi-functional filter device of claim 1, wherein the filter body and the dehumidifier sleeve are cylindrical.

20. The bi-functional filter device of claim 1, wherein the filter body and the dehumidifier sleeve comprise polyvinyl chloride (PVC) material.

21. The bi-functional filter device of claim 1, wherein an inner diameter of the filter body is $1\pm0.5$ millimeters, an outer diameter of the filter body is $3\pm1$ millimeters, and an outer diameter of the dehumidifier sleeve is $5\pm2$ millimeters.

22. The bi-functional filter device of claim 1, wherein the capillary path is helical.

23. The bi-functional filter device of claim 1, wherein the filter body comprises a helically coiled flat strip, the helically coiled flat strip forming a helicoidal strip structure (HSS) including multiple contiguous helical coil turns.

24. The bi-functional filter device of claim 23, wherein the helically coiled flat strip forms the through-channel in the filter body and the capillary path between the external surface and the inner wall of the filter body.

25. The bi-functional filter device of claim 23, wherein the capillary path comprises a helical spacing spiraling between, or defined by, the helical coil turns of the helicoidal strip structure (HSS).

26. The bi-functional filter device of claim 1, wherein the filter body is bi-directional with respect to a direction of a gas flowing in the through-channel.

27. A bi-functional filter device for a gas sampling line, comprising:
a filter body comprising:
a through-channel passing lengthwise through the filter body;
a capillary path providing a liquid flow path from the through-channel to a space external to the filter body, wherein the capillary path is configured to absorb liquids from the through-channel of the filter body by using capillary action; and
a dehumidifier sleeve enclosing the filter body, wherein the dehumidifier sleeve is configured to evaporate liquid contained in the filter body.

28. A gas sampling line for transferring gas from a gas source to a gas destination comprising:
a tube; and
a bi-functional filter device, the bi-functional filter device coupled to and in fluid communication with the tube, the bi-functional filter device comprising:
a filter body comprising:
an inner wall defining a through-channel that passes lengthwise through the filter body, and a capillary path providing a liquid flow path from the through-channel to a space external to the filter body; and a dehumidifier sleeve enclosing the filter body, wherein the dehumidifier sleeve is configured to evaporate liquid contained in the filter body.

* * * * *